US 7,041,624 B2

(12) United States Patent
Kober et al.

(10) Patent No.: US 7,041,624 B2
(45) Date of Patent: May 9, 2006

(54) BIOREGULATORY COMBINATION OF ACTIVE AGENTS

(75) Inventors: Reiner Kober, Fussgönheim (DE); Wilhelm Rademacher, Limburgerhof (DE); Jürgen Fries, Ludwigshafen (DE); Hans Ziegler, Mutterstadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/474,458

(22) PCT Filed: Apr. 12, 2002

(86) PCT No.: PCT/EP02/04119

§ 371 (c)(1),
(2), (4) Date: Oct. 8, 2003

(87) PCT Pub. No.: WO02/083732

PCT Pub. Date: Oct. 24, 2002

(65) Prior Publication Data

US 2004/0102322 A1    May 27, 2004

(30) Foreign Application Priority Data

Apr. 12, 2001    (DE) ............................. 101 18 458

(51) Int. Cl.
*A01N 33/12*    (2006.01)
*A01N 43/40*    (2006.01)
*A01N 43/653*   (2006.01)

(52) U.S. Cl. ..................................... 504/130; 504/139
(58) Field of Classification Search ............... 504/130, 504/139
See application file for complete search history.

(56) References Cited

U.S. PATENT DOCUMENTS

| 3,542,538 A | 11/1970 | Jung ............................. 71/76 |
| 3,905,798 A | 9/1975 | Zeeh et al. .................... 71/76 |
| 4,452,625 A | 6/1984 | Lurssen et al. ................ 71/76 |
| 4,532,341 A | 7/1985 | Holmwood et al. ........ 549/559 |
| 4,765,823 A | 8/1988 | Lurssen ......................... 71/92 |
| 6,455,470 B1 | 9/2002 | Parrish ....................... 504/130 |

FOREIGN PATENT DOCUMENTS

| DE | 3627404 | 2/1988 |
| DE | 19520935 | 12/1996 |
| EP | 199474 | 10/1986 |
| EP | 285880 | 10/1988 |
| EP | 287787 | 10/1988 |
| EP | 344533 | 12/1993 |
| EP | 831702 | 4/1998 |
| GB | 944807 | 12/1963 |
| GB | 2081700 | 2/1982 |
| GB | 2274102 | 7/1994 |

*Primary Examiner*—S. Mark Clardy
(74) *Attorney, Agent, or Firm*—Novak Druce DeLuca & Quigg, LLP

(57) ABSTRACT

The present invention relates to the use of specific quaternized bioregulatory active ingredients in combination with triazole derivatives, in particular metconazole or an agriculturally utilizable salt thereof. Corresponding compositions are likewise described.

23 Claims, No Drawings

BIOREGULATORY COMBINATION OF ACTIVE AGENTS

The present invention relates to the use of specific quaternized bioregulatory active ingredients in combination with triazole derivatives, in particular metconazole or an agriculturally utilizable salt thereof. Corresponding compositions are likewise described.

Bioregulatory active ingredients which are employed in the field of agriculture are, inter alia, quaternized compounds amongst which the most important representatives are N,N,N-trimethyl-N-β-chloroethylammonium chloride (CCC, chlorcholine chloride, chlormequat chloride, DE 12 94 734), N,N-dimethylmorpholinium chloride (DMC, DE 16 42 215) and N,N-dimethylpiperidinium chloride (DPC, MQC, mepiquat chloride, DE 22 07 575). These active ingredients, in particular chlormequat chloride and mepiquat chloride, are typically employed in the production of cereals at comparatively high dosage rates. The application rate of these active ingredients amounts, as a rule, to 0.3–1.5 kg/ha per application. The products are commercially available for example as aqueous active ingredient concentrates (for example Cycocel® and Terpal brands (mixtures with ethephon) in the form of SL mixtures, BASF).

Triazoles are an important class of active ingredients in the pesticide field. As ergosterol biosynthesis inhibitors, they are primarily employed as fungicides (see, for example, DE 195 20 935 A1). Some triazoles are also employed as plant growth regulators. In addition, various of the triazoles which, as such, have fungicidal activity are occasionally also described as having plant-growth regulatory properties (see, for example, EP 0 040 345 A2; EP 0 057 357 A2). Thus, paclobutrazole and uniconazole inhibit gibberellin biosynthesis and thus cell elongation and cell division.

The active ingredients from the class of the quaternized ammonium compounds can be employed together with other bioregulatory active compounds. For example, EP 0 344 533 describes synergistic combinations with growth-regulatory 3,5-dioxo-4-propionyl-cyclohexanecarboxylic acid derivatives such as prohexadione-calcium. DE 43 00 452 A1 proposes to employ CCC together with tebuconazole or triadimefon for inhibiting plant growth. The use of uniconazole together with CCC is described in EP 287 787 A1 for regulating plant growth.

However, the activity of the abovementioned active ingredients and active ingredient combinations is not satisfactory in specific cases. It is an object of the present invention to influence plant growth in a more effective manner.

We have found that this object is achieved by the present invention by the combined use of active ingredients from the class of the quaternized ammonium compounds and active ingredients from the triazole class, in particular the triazole derivative metconazole.

The present invention therefore relates to the use of at least one active ingredient of the formula (I)

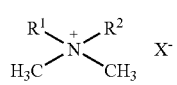
(I)

where $R^1$, $R^2$ and X have the following meanings:
$R^1$ is alkyl;
$R^2$ is alkyl, cyclopentenyl, haloalkyl; or where $R^1$ and $R^2$ together are a radical —(CH$_2$)$_5$—, —(CH$_2$)$_2$—O—(CH$_2$)$_2$— or —(CH$_2$)—CH=CH—(CH$_2$)—NH—;

X is an anionic group, in combination with metconazole, of the formula (II),

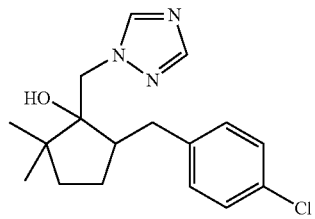
(II)

or an agriculturally utilizable salt thereof as bioregulator in plant production.

The use according to the invention of the active ingredient combination as bioregulator has advantages over the individual active substances in a series of a variety of applications in plant production, both in agriculture and in horticulture.

An example of a bioregulatory application is influencing the elongation of the aerial part of the plant (growth-regulatory). This extends to virtually all of the developmental stages of a plant.

Thus, for example, it is possible greatly to inhibit the vegetative growth of the shoot of plants, which manifests itself in particular in reduced elongation. Accordingly, the growth of the treated plants is stunted; also, the leaves are darker in colour. Advantageous for practice conditions are a reduced intensity of the growth of grasses on verges, hedges, canal embankments and on turf such as parks, sports grounds and orchards, ornamental lawns and airports, so that grass cutting, which is laborious and expensive, can be reduced. Also, more compact growth is desirable in a number of ornamental species.

Increasing the standing ability of crops which are prone to lodging, such as cereals, maize, oilseed rape and sunflowers, is also of economic interest. The shortened and strengthened stem axis reduces or eliminates the danger of "lodging" (breaking) of plants under adverse weather conditions before harvesting. Another important aspect is the growth-regulatory application for inhibiting elongation and for modifying the course of maturation over time in cotton. This makes possible completely automated harvesting of this crop plant. In fruit trees and other trees, pruning costs can be saved by means of growth regulation. At the same time, the ratio which is achieved between vegetative growth and fruit development is more advantageous. Moreover, biennial bearing of fruit trees may be avoided by means of growth regulation. Also, the growth-regulatory application may increase or inhibit lateral branching of the plants. This is of interest if, for example in tobacco plants, the development of side shoots (lateral shoots) is to be inhibited in order to favor foliar growth.

Also, frost hardness may be increased substantially by means of growth regulation, for example in the case of winter oilseed rape. Here, the vegetative development of the young rapeseed plants after sowing and before onset of winter frost is slowed down despite favorable growth conditions. Elongation and the development of too lush a foliar or plant biomass (which is therefore particularly sensitive to frost) are inhibited. Thus, the risk of frost damage of plants which tend to prematurely break down of floral inhibition and switch over to the generative phase is also reduced. In other crops too, for example in winter cereals, it is advantageous for the stands to be well into the tillering phase in autumn owing to plant-regulatory treatment, but to enter the cold season without unduly lush growth. This prevents increased sensitivity to subzero temperatures and—owing to the relatively low quantity of foliar biomass or plant biomass—attack by a variety of diseases (for example fungal disease). Moreover, inhibiting the vegetative growth makes possible denser planting of the soil in a number of crop plants so that higher yields based on the acreage can be achieved.

Moreover, higher yields both in terms of plant parts and in terms of plant constituents can be achieved by means of growth regulation. Thus, it is possible for example to induce the growth of larger amounts of buds, flowers, leaves, fruits, seed kernels, roots and tubers, to increase the sugar content in sugarbeet, sugarcane and citrus fruit, to increase the protein content in cereals or soya or to stimulate increased latex flux in rubber trees. In this context, the active ingredients may bring about increased yields by engaging in the plant metabolism or by promoting or inhibiting the vegetative and/or the generative growth. Finally, plant growth regulation may also bring about shortened or extended developmental stages or else an acceleration or delay in maturity of the harvested plant parts pre- or post-harvest.

Economically interesting is, for example, facilitated harvesting which is made possible by the concentration, over time, of the dehiscence or reduced adhesion to the tree in the case of citrus fruit, olives or in other varieties and cultivars of pome fruit, stone fruit and shelled fruit. The same mechanism, that is to say the promotion of the development of abscission tissue between, on the one hand, fruit or leaf portion and, on the other hand, the shoot portion of the plant, is also essential for a thoroughly controlled defoliation of useful plants such as, for example, cotton.

Moreover, growth regulation may bring about a reduction in the water consumption of plants. This is particulary important in the case of cropped areas which require artificial irrigation, which requires great financial input, for example in arid or semi-arid zones. Owing to the plant-regulatory application, the irrigation intensity may be reduced and farm economics improved. The effect of growth regulators may bring about better exploitation of the available water since, for example, the degree of stomatal opening is reduced, a thicker epidermis and cuticula are formed, root penetration into the soil is improved, the transpiring leaf surface area is reduced, or the microplant climate in the crop stand is advantageously affected by more compact growth.

The use according to the invention is particularly important for ornamentals, especially for fruit trees, and in particular for oilseed rape.

A particular subject matter of the present invention is the use of at least one active ingredient of the formula (I) in combination with at least one bioregulatory active ingredient from the triazole class as bioregulator for improving root growth. The purpose of this use is predominantly the development of an increased number of root branches, longer roots and/or an increased root surface area. This improves the water and nutrient uptake capacity of the plants. This is advantageous in particular in the case of light, for example sandy, soils and/or when there is a lack of precipitation. In autumn, a larger storage root is formed in particular in winter oilseed rape to allow for more intense new growth in spring. In spring, the improved root system provides better anchorage of the shoot in the ground so that the plants' standing ability is markedly improved. In other plants, the storage root constitutes all or the major part of the plant organ to be harvested (for example other Brassicaceae such as radish, but also sugarbeet, carrots or chicory).

Improved root growth is particularly advantageous when this is accompanied by a reduction of the vegetative growth, that is to say in particular with reduced shoot elongation (shortening) and/or reduction of the foliar biomass or plant biomass. Accordingly, the present use is advantageously directed at a reduction of the quotient of shoot biomass to root biomass.

This use, which is directed at the root development, takes place in particular in cereal production, for example for wheat, barley, oats and rye, also maize and rice, and very particularly in the case of plants which develop storage roots, such as Brassicacea, for example radish, predominantly oilseed rape and in particular winter oilseed rape, and sugarbeet, carrots or chicory. Oilseed rape production must be mentioned in particular in this context; this is where an improved root growth is particularly effective. In practice, this application, which is directed at the development of roots, may gain particular importance under specific circumstances, for example in the case of relatively dry soils and/or during the phase in which the plant develops the root system. With a simultaneous reduction of the shoot elongation, the improved root growth is particularly advantageous.

The invention thus relates to the use of bioregulatory active ingredient combinations. The use according to the invention is a combined application, i.e. the use of at least one active ingredient of the formula (I)—hereinbelow referred to as "active ingredient component (a)" for the sake of simplicity—and the use of triazole derivatives, in particular metconazole, of the formula (II), or an agriculturally utilizable salt thereof—hereinbelow referred to as "active ingredient component (b)" for the sake of simplicity—is effected in a context to suit the intended purpose, in particular with regard to optimum efficacy. Thus, the active ingredient components (a) and (b) may in principle be applied jointly in one formulation (ready-to-use formulation) or separately in at least two independent formulations. The application of separate formulations comprises not only the simultaneous application, i.e. the application at essentially the same points in time or immediately in succession, but also the staggered application, i.e. application at different points in time. As a rule, simultaneous application is preferred.

Particular active ingredients of the formula (I) result when alkyl is methyl, ethyl, isopropyl. The 2-chloroethyl group is the preferred haloalkyl group. If the substituents together with the nitrogen atom to which they are bonded form a cyclic radical, $R^1$ and $R^2$ are preferably a morpholino or piperidino group. $X^-$ is, for example, a halide such as bromide and preferably chloride; sulfate; an alkyl sulfate such as methyl sulfate; an alkylsulfonate, such as methylsulfonate; a borate such as pentaborate; or another anionic group which is utilizable in agriculture. In principle, divalent anionic groups are also suitable; these are employed in corresponding stoichiometric amounts relative to the ammonium cation.

In particular borates, $X^-$ is an anion of the formula (III)

$$1/m \cdot [M_x B_y O_z (A)_v]^{m-} \cdot w(H_2O) \qquad \text{(III)}$$

where

M is a cation of an agriculturally utilizable metal, hydrogen or ammonium;

B is boron;

O is oxygen;

A is a chelating or complexing group which is associated with at least one boron atom or an agriculturally utilizable cation;

x corresponds to a number of from 0 to 10;
y corresponds to a number of from 1 to 48;
v corresponds to a number of from 0 to 24;
z corresponds to a number of from 0 to 48;
m corresponds to an integer of from 1 to 6;
w corresponds to a number of from 0 to 24.

Preferred borates of the formula (III) are those where x is zero; or
M is sodium, potassium, magnesium, calcium, zinc, manganese, copper, hydrogen or ammonium; and/or
y corresponds to a number of from 2 to 20, 2 to 10 or 3 to 10; and/or
m is 1 or 2; and/or
w corresponds to a number of from 0 to 24.

Especially preferred borates of the formula (III) are those where y corresponds to a number of from 3 to 7, in particular 3 to 5;
z corresponds to a number of from 6 to 10, in particular 6 to 8;
v is zero;
w corresponds to a number of from 2 to 10, in particular 2 to 8.

Very especially preferred borates of the formula (III) are those where y=5; z=8; v=0; m=1; w=2 to 3 (pentaborates).

If present, chelating and complexing groups A are preferably selected from among hydroxycarboxylic acids, carboxylic acids, alcohols, glycols, aminoalcohols, sugars and the like compounds.

Moreover, the borates may contain water, for example in the form of water of crystallization in free or coordinated form or as bound water in the form of hydroxyl groups which are bound to the boron.

Further embodiments and also the preparation of borates according to the invention, which is known per se, are described in PCT/EP98/05149.

The active ingredient of the formula I is preferably selected from among (a1) N,N,N-trimethyl-N-β-chloroethylammonium salts of the formula (Ia),

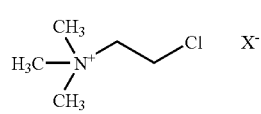
(Ia)

(a2) N,N-dimethylpiperidinium salts of the formula (Ib) and

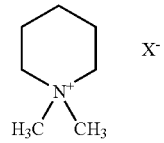
(Ib)

(a3) N,N-dimethylmorpholinium salts of the formula (Ic)

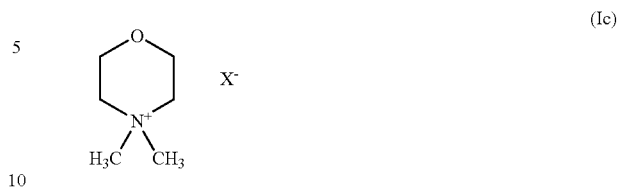
(Ic)

where $X^-$ is in particular $Cl^-$ or $1/m \cdot [M_xB_yO_z(A)_v]^{m-} \cdot w\,(H_2O)$ with the abovementioned meanings.

Especially preferred are the active ingredient components (a1) and/or (a2), in particular N,N,N-trimethyl-N-β-chloroethyl-ammonium chloride (CCC) or the corresponding pentaborate, or N,N-dimethylpiperidinium chloride (MQC) or the corresponding pentaborate.

In one embodiment of the present invention, the active ingredient component (a) consists essentially of a compound of the formula (Ia) or (Ib) or a mixture of these.

The active ingredients from the triazole class which have suitable bioregulatory activity include in particular (b1) metconazole, (b2) triadimenol, (b3) triadimefon, (b4) cyproconazole, (b5) tebuconazole, (b6) uniconazoles, (b7) paclobutrazole and (b8) ipconazole. Those which are preferably used, mainly with regard to improvement of root growth in accordance with the invention, are (b1), (b5) and/or (b8).

Preferred in accordance with the invention is the use of (b1) metconazole, of the formula (II),

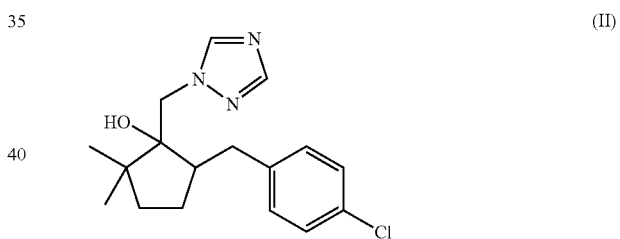
(II)

or of an agriculturally utilizable salt thereof.

The representation of metconazole of the formula (II) which has been chosen here includes isomeric forms of these compounds. Those which must be mentioned in particular are stereoisomers, such as enantiomers or diastereoisomers of the formulae (IIa–d). Besides the essentially pure isomers, the compounds of the formulae (II) also include their isomer mixtures, for example stereoisomer mixtures. A high proportion of cis isomers is preferred, advantageously with a cis:trans ratio of 5:1 to 20:1.

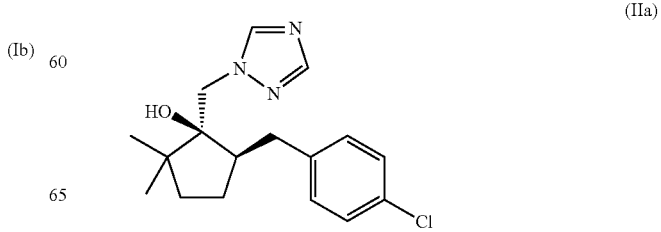
(IIa)

-continued

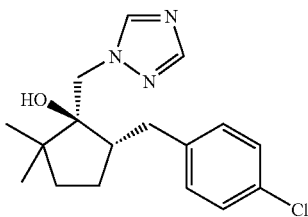

(IIb)

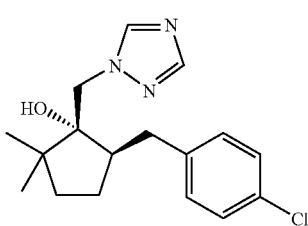

(IIc)

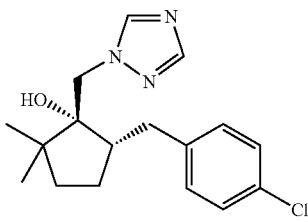

(IId)

In the present case, the agriculturally utilizable metconazole salts are preferably acid addition salts.

Anions of useful acid addition salts are predominantly chloride, bromide, fluoride, hydrogen sulfate, sulfate, dihydrogen phosphate, hydrogen phosphate, phosphate, nitrate, hexafluorosilicate, hexafluorophosphate.

In one embodiment of the present invention, the active ingredient component (b) essentially consists of (b1), i.e. of a compound of the formula (II). In accordance with a further embodiment, the active ingredient component (b) essentially consists of a compound selected among (b1) to (b8), or a mixture of these.

In a particular embodiment, N,N,N-trimethyl-N-β-chloroethylammonium chloride of the formula (Ia) or N,N-dimethylpiperidinium chloride of the formula (Ib) is used in combination with metconazole, of the formulae (II).

In addition to the active ingredient components (a) and (b), the use according to the invention may involve further active ingredients. These active ingredients may in particular take the form of those whose activity resembles the activity mediated by the active ingredients of the formula (I) or active ingredients from the triazole class, or which complements this activity. Thus, it may be advantageous additionally to the combination according to the invention to employ further bioregulators, in particular ethephon, prohexadione-calcium or trinexapac-ethyl, but also herbicides, in particular imazaquin, and fungicides. Vitamins, cofactors, trace elements, in particular B, Cu, Co, Fe, Mn, Mo and Zn, minerals, amino acids and other essential nutrients may also be expedient.

The application rates of individual active ingredients which are required per se for bioregulation purposes can advantageously be reduced within the context of the combined application according to the invention. Thus, the application rate of active ingredients of the formula (I) can be set at less than 500 g and preferably less than 350 g per ha and the application rate of metconazole, of the formula (II), or of agriculturally utilizable salts thereof at less than 100 g and preferably less than 50 g and in particular less than 30 g per ha.

In context with the treatment, the use according to the invention of the active ingredients which have been described includes a method. In this method, an effective amount of active ingredient component (a) and an effective amount of active ingredient component (b), as a rule formulated to meet the requirements of agricultural practice, is applied to the area under cultivation to be treated. The active ingredient components are preferably fed to the plant as a foliar spray.

For application purposes, the active ingredient components according to the invention may be formulated in the manner known per se, for example as liquid formulations such as emulsifiable concentrates (EC), suspoemulsions (SE), oil-in-water emulsions (EW), water-in-oil emulsions (EO), aqueous suspension concentrates and oil suspension concentrates (SC), microemulsions (ME), water-soluble concentrates (SL), and solid formulations such as water-dispersible powders (WP), water-dispersible granules (WG), water-soluble powders (SP), water-soluble granules (SG) and the like. Liquid/aqueous systems are preferred. If the active ingredients of the formula (I) are used in the form of the above-described boron salts, solid formulations are also advantageous.

In most cases, the compositions are formulated in such a manner that they need to be prepared in a suitable manner prior to use by the user, which is, as a rule, the farmer, in a manner known per se. For example, it may be necessary to dilute a suitable active ingredient concentrate with water to give the desired concentration or to process it with water to give a ready-to-use spray mixture.

Sprayable mixtures normally comprise 0.0001 to 10% by weight, preferably 0.001 to 5% by weight, and in particular 0.002 to 2.0% by weight, of active ingredient component (a) and/or (b). To prepare a customary spray mixture, for example 0.2 to 5.0 l, preferably 0.3 to 3.0 l and in particular 0.35 to 2.0 l of an active ingredient concentrate comprising component (a) and/or (b) may be diluted with water down to 10 to 2 000 l, preferably 50 to 500 l and in particular 100 to 1 000 l. If appropriate, 0.1% by weight to 5% by weight (based on the spray mixture) of further anionic, cationic or nonionic surfactants, adjuvants, polymers and/or further active ingredients are added to the spray mixture. Examples of substances for such surfactants and further adjuvants are described hereinbelow. Those which must be mentioned in particular are starch and starch derivatives, for example a carboxyl and sulfonyl-containing starch (Nu-Film from Union Carbide Corp.) and spreaders and extenders, such as Vapor Guard from Miller Chemical & Fertilizer Corp.

The compositions can be applied in the manner known per se, for example by spraying the spray mixtures with a mobile sprayer, using nozzles with ultrafine distribution. The apparatuses and procedures customary for this purpose are known to the skilled worker.

The invention thereore also relates to compositions and to the preparation of compositions for the treatment of plants.

Accordingly, the present invention furthermore relates to compositions comprising (a) at least one active ingredient of the formula (I)

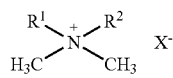
(I)

where $R^1$, $R^2$ and X have the abovementioned meanings; and (b) metconazole, of the formula (II),

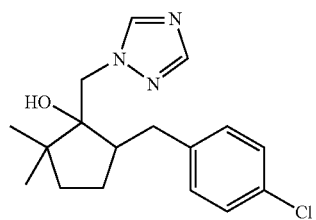
(II)

or an agriculturally utilizable salt thereof.

A particular embodiment of this subject matter are compositions with high active ingredient concentrations (concentrates). In this case, component (a) may amount to more than 5% by weight, preferably more than 10% by weight and in particular more than 20% by weight of the total weight of the composition. On the other hand, as a rule, it is advantageous for component (a) to amount to less than 50% by weight, preferably less than 40% by weight and in particular less than 35% by weight of the total weight of the composition. In the case of concentrates, component (b) may amount to more than 0.5% by weight, preferably more than 1% by weight and in particular more than 2% by weight of the total weight of the composition. On the other hand, as a rule, it is advantageous for component (b) to amount to less than 20% by weight, preferably less than 10% by weight and in particular less than 5% by weight of the total weight of the composition.

The relative active ingredient contents in combination products and also when applied separately vary within a wide range. According to one aspect, relatively higher amounts by weight of active ingredient component (a) than active ingredient component (b) are employed. This weight ratio of (a) to (b) is typically within a range of from 5:1 to 30:1, preferably 7:1 to 25:1 and in particular 10:1 to 20:1. This applies in particular to the use of metconazole.

In a particular embodiment, compositions according to the invention comprise at least one further plant active ingredient, for example, herbicides, fungicides, bioregulators, as component (c).

In the case of concentrates, the active ingredient content as the total of components (a), (b) and (c) as a rule amounts to more than 20% by weight, preferably more than 25% by weight and in particular more than 30% by weight of the total weight of the composition. On the other hand, the active ingredient content as the total of components (a), (b) and (c) as a rule amounts to less than 70% by weight, preferably less than 60% by weight and in particular less than 50% by weight of the total weight of the composition.

If appropriate, the compositions comprise a further bioregulator, in particular ethephon, prohexadione-calcium, or trinexapac-ethyl, as component (c1).

If present, component (c1) amounts as a rule to 1 to 40% by weight of the total weight of the composition.

In a particular embodiment of the present invention, the compositions comprise not only the active ingredient components (a) and (b), but also the active ingredient component (c1), in particular chlormequat chloride and/or mepiquat chloride and/or the corresponding borates of the formulae (Ia) or (Ib) and metconazole, of the formula (II), together with ethephon and advantageously with trinexapac-ethyl.

In a particular embodiment of the present invention, the compositions comprise at least one surfactant as surface-active component (d). In this context, the term "surfactant" refers to boundary-active or surface-active agents.

Depending on the type of formulation, component (d) acts predominantly as dispersing agent or emulsifier. Moreover, at least parts of component (d) may act as wetter.

Substances which may be used in principle are nonionic, anionic, cationic and amphoteric surfactants, the hydrophobic group including polymer surfactants and surfactants containing hetero atoms.

If present, component (d) amounts as a rule to 5 to 60% by eight, preferably 10 to 50% by weight and in particular 20 to 40% by weight of the total weight of the composition.

In a particular embodiment of the present invention, the compositions comprise at least one further adjuvant as component (e).

Component (e) may have a variety of purposes. Suitable adjuvants are usually selected by the skilled worker to meet the requirements.

For example, further adjuvants are selected from among (e1) minerals and trace elements which can be utilized by the plant;

(e2) further solvents or diluents;

The minerals and trace elements which can be utilized by plants include in particular inorganic ammonium salts such as ammonium sulfate, ammonium nitrate, ammonium chloride, ammonium phosphate, or further minerals or trace elements which can be utilized by plants, in particular ammonium nitrate fertilizer granules and/or urea. They may be introduced into the compositions according to the invention for example in the form of aqueous concentrates, if appropriate concentrate blends, such as, for example, Ensol solutions.

If present, component (e1) as a rule amounts to up to 40% by weight, preferably up to 30% by weight and in particular up to 20% by weight of the total weight of the composition.

As a rule, the compositions according to the invention comprise water. The water acts predominantly as a solvent for the active ingredient component (a). As a rule, it is expedient for the water to amount to approximately 30 to 70% by weight of the weight of component (a).

Besides water, the compositions may comprise further solvents for soluble constituents or diluents for insoluble constituents of the composition. In particular metconazole, which per se is only sparingly soluble in water, can be incorporated homogeneously into the formulation in this manner.

Substances which can be used in principle are, for example, mineral oils, synthetic oils and vegetable and animal oils, or else low-molecular-weight hydrophilic solvents such as alcohols, ethers, ketones and the like.

If present, the above-described further solvents or diluents as a rule amount to less than 30% by weight, preferably less than 20% by weight and in particular less than 15% by weight of the total weight of the composition.

Further additions which may be useful are found for example among mineral salt solutions, which are employed for alleviating nutritional deficiencies and trace element deficiencies, nonphytotoxic oils and oil concentrates, antidrift reagents, antifoams, in particular those of the silicone type, for example Silicon SL, which is commercially available from Wacker, and the like.

In a particular embodiment, the present invention relates to aqueous compositions comprising
 (a) 10 to 70% by weight of at least one active substance selected from among (a1) N,N,N-trimethyl-N-β-chloroethylammonium chloride, of the formula (Ia), and (a2) N,N-dimethylpiperidinium chloride of the formula (Ib) or the corresponding borates;
 (b) 0.5 to 20% by weight, preferably 1 to 10% by weight and in particular 2 to 5% by weight of at least one active ingredient of the triazole class and in particular metconazole, of the formula (II), or of an agriculturally useful salt thereof.

For the purposes of the present description, quantites are generally based on the total weight of the composition, unless otherwise specified. In accordance with the invention, the term "essentially" as a rule refers to a percentage ratio of at least 90%, preferably of at least 95% and in particular of at least 98%.

Compositions according to the invention can be prepared in a manner known per se. To this end, at least some components are combined. It must be taken into consideration that products, in particular commercially available products, whose constituents may contribute to various components may be used. For example, a specific surfactant may be dissolved in an aprotic solvent so that this product may contribute to a variety of components. Furthermore, small amounts of substances which are undesired per se may be introduced with commercially available products.

For example, the active ingredients may be mixed with the additives as solids or in the form of aqueous highly concentrated products. Preferably, for example aqueous active ingredient solutions of the quaternized active ingredients of the formula I are initially introduced at a concentration of from 50 to 80% by weight and the additives are then incorporated with stirring. The mixture may subsequently be treated with a concentrate of triazole active ingredients, in particular a metconazole concentrate, in a suitable solvent.

Mixing may be effected in a manner known per se, for example by homogenizing using suitable devices such as KPG stirrers or magnetic stirrers, or the corresponding large-scale stirrers.

Within the scope of the present invention, terms such as alkyl, alkoxy and the like encompass straight-chain or branched hydrocarbon groups such as methyl, ethyl, n-propyl, i-propyl, n-butyl, i-butyl, sec-butyl, t-butyl, n-pentyl, n-hexyl, n-octyl, 2-ethylhexyl, n-nonyl, iso-nonyl, n-decyl, iso-decyl, n-undecyl, iso-undecyl, n-dodecyl, iso-dodecyl, n-tridecyl, iso-tridecyl, stearyl, n-eicosyl, preferably—unless otherwise specified—with 1 to 8, in particular 1 to 6 and especially preferably 1 to 4 carbon atoms.

The term "halogen" preferably represents fluorine, chlorine, bromine and iodine, in particular fluorine and especially chlorine.

The invention is illustrated in greater detail by the examples which follow:

PREPARATION EXAMPLES

Reference Example 1

Formulations

The tank mixes employed in Example 1 are prepared by stirring an emulsion concentrate comprising 90 g/l metconazole, of the formula (II), and an aqueous concentrate comprising 600 g/l mepiquat chloride (MQC) using a magnetic stirrer.

The formulations employed in Example 2 are prepared by introducing an emulsion concentrate comprising 60 g/l metconazole, of the formula (II), and/or an aqueous concentrate comprising 460 g/l mepiquat chloride in suitable amounts. The combination of mepiquat chloride and metconazole is employed in the form of an aqueous SL readymix comprising 21 g/l metconazole, 300 g/l mepiquat chloride and 610 g/l further formulation auxiliaries.

Examples 1

Biological Activity (Shoot Elongation)

Winter oilseed rape (cv. Pronto) was sown in autumn (Sep. 13, 2000) and treated approximately one month later (Oct. 19, 2000) in accordance with the information given in Table 1. A few weeks later, the shoot elongation and the root development were assessed (A1 on Oct. 26, 2000 and A2 on Nov. 16, 2000). The results of the elongation are compiled in Table 1.

TABLE 1

Shoot elongation in winter oilseed rape (rating A1 and A2)

| Active ingredient | [g/ha] | Stage A1: rel. length | Reduction [%] | Stage A2: rel. length | Reduction [%] |
|---|---|---|---|---|---|
| MQC | 400 | 100 | 0 | 96 | 4 |
| Metconazole | 21 | 81 | 19 | 61 | 39 |
| MQC + metconazole | 400 + 21 | 75 | 25 | 54 | 46 |

The expected reduction, which was calculated using Colbi's formula, was 19% for rating A1 and 41.4% for rating A2. The reductions found for the active ingredient combination according to the invention were 25% and 46%, respectively, and confirm the synergism.

Examples 2

Biological Activity (Root Growth)

Winter oilseed rape (cv. Pronto) was sown in autumn (Sep. 13, 2000) and treated approximately one month later (Oct. 19, 2000) in accordance with the information given in Table 2. Some of the plants were harvested in autumn on Dec. 7, 2000, while others were harvested in spring on Apr. 3, 2001 and the following morphological parameters were analyzed: plant length; shoot fresh and dry weight (drying: 24 h at 105° C.); total area of all leaves; SPAP (relative units of green coloration determined using a Minolta chlorophyll-measuring meter SPAP 502); root fresh and dry weight (drying: 24 h at 105° C.); storage root fresh weight; length, surface area and volume of the hair roots, and number of root tips (scanning and WinRhizo determination). The results, each of which is based on the untreated control, are compiled in Table 2, the values for the plants harvested in autumn being shown first and the values for the plants harvested in spring being shown second.

TABLE 2

Root growth in winter oilseed rape

| Active ingredient | [g/ha] | Total root fresh weight [%] | Total root dry weight [%] | Storage root fresh weight [%] | Root hair length [%] |
|---|---|---|---|---|---|
| Control | — | 100; 100 | 100; 100 | 100; 100 | 100; 100 |
| MQC | 400 | 123; 112 | 120; 107 | 118; 94 | 112; 123 |
| Metconazole | 28 | 92; 115 | 94; 128 | 94; 115 | 107; 126 |
| Metconazole | 84 | 78; 150 | 75; 161 | 74; 138 | 94; 129 |
| MQC + metconazole (readymix) | 400 + 28 | 128; 141 | 123; 146 | 111; 137 | 145; 130 |

| Active ingredient | [g/ha] | Hair root surface area [%] | Hair root volume [%] | Number of root tips [%] | Plant height [%] |
|---|---|---|---|---|---|
| Control | — | 100; 100 | 100; 100 | 100; 100 | 100; 100 |
| MQC | 400 | 131; 136 | 154; 157 | 94; 123 | 96; 93 |
| Metconazole | 28 | 116; 134 | 125; 145 | 93; 112 | 61; 91 |
| Metconazole | 84 | 97; 148 | 101; 183 | 87; 116 | 46; 86 |
| MQC + metconazole (readymix) | 400 + 28 | 164; 144 | 186; 173 | 122; 123 | 36; 83 |

| Active ingredient | [g/ha] | Shoot fresh weight [%] | Shoot dry weight [%] | Leaf surface area [%] | SPAD |
|---|---|---|---|---|---|
| Control | — | 100; 100 | 100; 100 | 100; 100 | 100; 100 |
| MQC | 400 | 111; 114 | 112; 99 | 116; 103 | 102; 102 |
| Metconazole | 28 | 82; 122 | 85; 112 | 84; 106 | 107; 103 |
| Metconazole | 84 | 57; 150 | 67; 136 | 61; 127 | 116; 104 |
| MQC + metconazole (readymix) | 400 + 28 | 83; 113 | 85; 101 | 81; 108 | 119; 108 |

When the treatment was carried out with the active ingredient combination according to the invention, an increased number of individual roots, longer roots and/or an increased root surface area were observed in comparison with the individual active ingredients. In particular, it emerged that the treatment in accordance with the invention leads a shoot biomass/root biomass ratio which is comparably more favorable for overwintering and for vigorous regrowth of the plant in spring.

We claim:

1. A method for bioregulation in plant production, which comprises applying at least one active ingredient (I) selected from the group consisting of
(a1) N,N,N-trimethyl-N-β-chloroethylammonium salts of the formula (Ia),

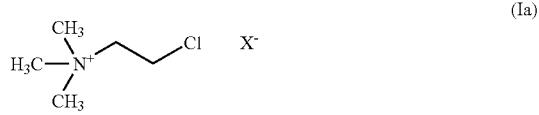

(a2) N,N-dimethylpiperidinium salts of the formula (Ib)

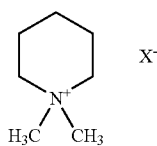

wherein
X is an anionic group, in combination with metconazole, of the formula (II)

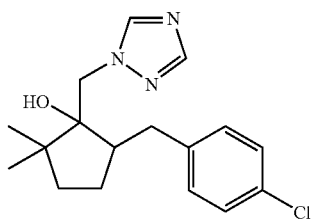

or an agriculturally utilizable salt thereof.

2. The method as claimed in claim 1, wherein
$X^-$ is $Cl^-$ or $1/m \cdot [M_xB_yO_z(A)_v]^{m-} \cdot w\,(H_2O)$, where
M is a cation of an agriculturally utilizable metal, hydrogen or ammonium;
B is boron;
O is oxygen;
A is a chelating or complexing group which is associated with at least one boron atom or an agriculturally utilizable cation;
x corresponds to a number of from 0 to 10;
y corresponds to a number of from 1 to 48;
v corresponds to a number of from 0 to 24;
z corresponds to a number of from 0 to 48;
m corresponds to an integer of from 1 to 6;
w corresponds to a number of from 0 to 24.

3. The method as claimed in claim 1, wherein the active ingredient (I) is N,N,N-trimethyl-N-β-chloroethylammonium chloride of the formula (Ia) or N,N-dimethylpiperidinium chloride of the formula (Ib).

4. The method as claimed in claim 1, wherein $X^-$ is $Cl^-$ or is $[M_xB_yO_z(A)_v]^{m-} \cdot w\,(H_2O)$, where x=zero, y=5, z=8, v=zero, m=1 and w=2 to 3.

5. The method as claimed in claim 1, wherein the application rate of active ingredients (I) amounts to less than 500 g per ha.

6. The method as claimed in claim 5, wherein the application rate of active ingredients (I) amounts to less than 350 g per ha.

7. The method as claimed in claim 1, wherein the application rate of metconazole, of the formula (II), or of agriculturally utilizable salts thereof amounts to less than 100 g per ha.

8. The method as claimed in claim 7, wherein the application rate of metconazole, of the formula (II), or of agriculturally utilizable salts thereof amounts to less than 50 g per ha.

9. The method as claimed in claim 1, wherein the plant production is the production of oilseed rape.

10. The method as claimed in claim 1, wherein the active ingredient (I) is N,N-dimethylpiperidinium chloride.

11. The method as claimed in claim 1, wherein the active ingredient (I) and the metconazole or the agriculturally utilizable salt thereof are applied in synergistically effective amounts.

12. The method as claimed in claim 1, for improving root growth.

13. The method as claimed in claim 12, wherein the improvement of root growth is manifested in an increased number of root branches, in longer roots and/or in an increased root surface area.

14. The method as claimed in claim 12, wherein the roots are roots of oilseed rape.

15. The method as claimed in claim 12, wherein the application rate of active ingredients (I) amounts to less than 500 g per ha.

16. The method as claimed in claim 15, wherein the application rate of active ingredients (I) amounts to less than 350 g per ha.

17. The method as claimed in claim 12, wherein the application rate of metconazole, or of the agriculturally utilizable salts thereof amounts to less than 100 g per ha.

18. The method as claimed in claim 17, wherein the application rate of metconazole, or of the agriculturally utilizable salts thereof amounts to less than 50 g per ha.

19. A composition comprising
(a) at least one active ingredient (I) selected from the group consisting of
(a1) N,N,N-trimethyl-N-β-chloroethylammonium salts of the formula (Ia),

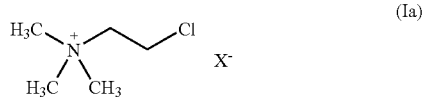

(a2) N,N-dimethylpiperidinium salts of the formula (Ib)

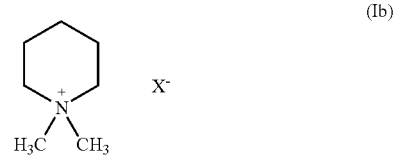

wherein
X is an anionic group; and
(b) metconazole, of the formula (II)

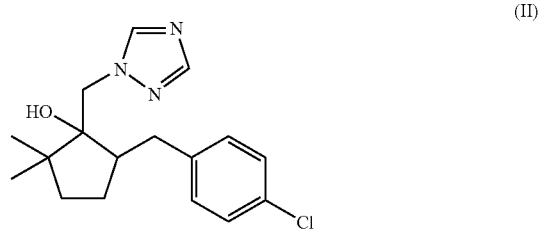

or an agriculturally utilizable salt thereof.

20. The composition as claimed in claim 19, wherein the active ingredient (I) is N,N-dimethylpiperidinium chloride.

21. The composition as claimed in claim 19, which comprises the active ingredient (I) and the metconazole or the agriculturally utilizable salt thereof in synergistically effective amounts.

22. The composition as claimed in claim 19, wherein $X^-$ is $Cl^-$ or $1/m \cdot [M_xB_yO_z(A)_v]^{m-} \cdot w\,(H_2O)$, and M is a cation of an agriculturally utilizable metal, hydrogen or ammonium;

B is boron;

O is oxygen;

A is a chelating or complexing group which is associated with at least one boron atom or an agriculturally utilizable cation;

x corresponds to a number of from 0 to 10;

y corresponds to a number of from 1 to 48;

v corresponds to a number of from 0 to 24;

z corresponds to a number of from 0 to 48;

m corresponds to an integer of from 1 to 6;

w corresponds to a number of from 0 to 24.

23. The composition as claimed in claim 22, wherein $X^-$ is $Cl^-$ or is $[M_xB_yO_z(A)_v]^{m-} \cdot w\,(H_2O)$, and x=zero, y=5, z=8, v=zero, m=1 and w=2 to 3.

* * * * *